(12) United States Patent
McGhee et al.

(10) Patent No.: US 10,178,927 B2
(45) Date of Patent: Jan. 15, 2019

(54) SYSTEM AND METHOD FOR SENSING OIL QUALITY

(71) Applicant: Pitco Frialator, Inc., Concord, NH (US)

(72) Inventors: Owen R. McGhee, Raymond, NH (US); Selim A. Bassoul, Elgin, IL (US); Jason D. Finnie, Bow, NH (US); Jared Perkins, Chester, NH (US); Nathaniel A. Lambert, Hookset, NH (US); Michael T. Fecteau, Derry, NH (US)

(73) Assignee: Pitco Frialator, Inc., Concord, NH (US)

( * ) Notice: Subject to any disclaimer, the term of this patent is extended or adjusted under 35 U.S.C. 154(b) by 0 days.

(21) Appl. No.: 15/863,197

(22) Filed: Jan. 5, 2018

(65) Prior Publication Data

US 2018/0125299 A1    May 10, 2018

Related U.S. Application Data

(63) Continuation of application No. 14/752,278, filed on Jun. 26, 2015, now Pat. No. 9,861,233.

(Continued)

(51) Int. Cl.
*A47J 37/12* (2006.01)
*G01N 33/03* (2006.01)

(52) U.S. Cl.
CPC .......... *A47J 37/1266* (2013.01); *G01N 33/03* (2013.01)

(58) Field of Classification Search
CPC ........................................ A47J 37/12–37/1295

(Continued)

(56) References Cited

U.S. PATENT DOCUMENTS 4,148,729 A    4/1979   Howard
4,210,123 A    7/1980   Moore et al.
(Continued)

FOREIGN PATENT DOCUMENTS

CN    2789764 Y    6/2006
CN    203060962 U    7/2013
(Continued)

OTHER PUBLICATIONS

Communication Under Rule 71(3) EPC for Application No. 15 815 092.0, dated Oct. 8, 2018, 36 pp.

(Continued)

*Primary Examiner* — Michael Laflame, Jr.
(74) *Attorney, Agent, or Firm* — Brinks Gilson & Lione

(57) ABSTRACT

A system for measuring the state of degradation of cooking oil in a deep fryer is provided. The system includes at least one fryer pot and a loop of piping fluidly connected thereto for selectively allowing flow of oil from the at least one fryer pot into the loop and for selectively allowing the cooking oil to return to said at least one fryer pot from the loop. A pump urges the flow of cooking oil through the loop of piping and selectively to urge oil to return to the at least one fryer pot. The loop further comprises a return portion that extends from a discharge of the pump toward a suction of the pump. A sensor is disposed in the return portion of the loop and adapted to measure an electrical property that is indicative of total polar materials of said cooking oil.

17 Claims, 4 Drawing Sheets

Related U.S. Application Data

(60) Provisional application No. 62/019,136, filed on Jun. 30, 2014.

(58) Field of Classification Search
USPC ............ 99/403–418; 324/600, 649, 691, 693
See application file for complete search history.

(56) References Cited

U.S. PATENT DOCUMENTS

| | | |
|---|---|---|
| 4,324,173 A | 4/1982 | Moore et al. |
| 4,487,691 A | 12/1984 | Panora |
| 4,506,995 A | 3/1985 | Polster |
| 4,688,475 A | 8/1987 | Witt et al. |
| 4,742,455 A | 5/1988 | Schreyer |
| 4,764,258 A | 8/1988 | Kauffman |
| 4,908,676 A | 3/1990 | Bedell et al. |
| 4,959,144 A | 9/1990 | Bernard |
| 4,974,405 A | 12/1990 | Littau |
| 5,071,527 A | 12/1991 | Kauffman |
| 5,160,444 A | 11/1992 | McFarland |
| 5,179,891 A | 1/1993 | Chiu |
| 5,239,258 A | 8/1993 | Kauffman |
| 5,247,876 A | 9/1993 | Wilson et al. |
| 5,404,799 A | 4/1995 | Bivens |
| 5,523,692 A | 6/1996 | Kuroyanagi et al. |
| 5,594,327 A | 1/1997 | Sagredos et al. |
| 5,617,777 A | 4/1997 | Davis et al. |
| 5,776,530 A | 7/1998 | Davis et al. |
| 5,787,372 A | 7/1998 | Edwards et al. |
| 5,818,731 A | 10/1998 | Mittal et al. |
| 5,929,754 A | 7/1999 | Park et al. |
| 5,933,016 A | 8/1999 | Kauffman et al. |
| 5,942,269 A | 8/1999 | Casey et al. |
| 5,951,854 A | 9/1999 | Goldberg et al. |
| 5,954,933 A | 9/1999 | Ingalls et al. |
| 6,009,974 A | 1/2000 | Casey et al. |
| 6,127,185 A | 10/2000 | Melton et al. |
| 6,132,782 A | 10/2000 | Burkett et al. |
| 6,235,210 B1 | 5/2001 | Saksena |
| 6,274,850 B1 | 8/2001 | Mercer |
| 6,278,282 B1 | 8/2001 | Marszalek |
| 6,378,420 B1 | 4/2002 | Savage et al. |
| 6,436,713 B1 | 8/2002 | Onwumere et al. |
| 6,455,085 B1 | 9/2002 | Duta |
| 6,459,995 B1 | 10/2002 | Collister |
| 6,469,521 B1 | 10/2002 | Klun et al. |
| 6,553,812 B2 | 4/2003 | Park et al. |
| 6,600,306 B1 | 7/2003 | Pernot et al. |
| 6,602,533 B1 | 8/2003 | Smith et al. |
| 6,717,667 B2 | 4/2004 | Abraham et al. |
| 6,745,669 B2 | 6/2004 | Suzuki |
| 6,777,009 B1 | 8/2004 | Shealy |
| 6,783,685 B2 | 8/2004 | Hwang |
| 6,791,334 B2 | 9/2004 | Horie et al. |
| 6,822,461 B2 | 11/2004 | Klun |
| 6,873,916 B2 | 3/2005 | Kolosov et al. |
| 6,958,166 B2 | 10/2005 | Taylor |
| 7,019,654 B2 | 3/2006 | Danyluk et al. |
| 7,030,629 B1 | 4/2006 | Stahlmann et al. |
| 7,043,967 B2 | 5/2006 | Kauffman et al. |
| 7,043,969 B2 | 5/2006 | Matsiev et al. |
| 7,129,715 B2 | 10/2006 | Hayashi et al. |
| 7,132,079 B2 | 11/2006 | Onwumere et al. |
| 7,158,897 B2 | 1/2007 | Kolosov et al. |
| 7,210,332 B2 | 5/2007 | Kolosov et al. |
| 7,225,081 B2 | 5/2007 | Kolosov et al. |
| 7,239,155 B2 | 7/2007 | Byington et al. |
| 7,254,990 B2 | 8/2007 | Matsiev et al. |
| 7,287,431 B2 | 10/2007 | Liu et al. |
| 7,383,731 B2 | 6/2008 | Liu et al. |
| 7,390,666 B2 | 6/2008 | Onwumere et al. |
| 7,407,566 B2 | 8/2008 | Jiang et al. |
| 7,504,835 B2 | 3/2009 | Byington et al. |
| 7,504,836 B2 | 3/2009 | Chambon et al. |
| 7,521,945 B2 | 4/2009 | Hedges et al. |
| 7,523,006 B2 | 4/2009 | Muhl et al. |
| 7,523,646 B2 | 4/2009 | Klun |
| 7,600,424 B2 | 10/2009 | Sasaki et al. |
| 7,652,490 B2 | 1/2010 | Muhl et al. |
| 7,719,289 B2 | 5/2010 | Muhl et al. |
| 7,729,870 B2 | 6/2010 | Sun |
| 7,834,646 B2 | 11/2010 | Chambon et al. |
| 7,928,741 B2 | 4/2011 | Hedges et al. |
| 8,207,749 B2 | 6/2012 | Reime |
| 8,257,976 B2 | 9/2012 | Wei et al. |
| 8,287,182 B2 | 10/2012 | Muhl et al. |
| 8,325,345 B2 | 12/2012 | Mahmoodi et al. |
| 8,340,928 B2 | 12/2012 | Sun |
| 8,421,486 B2 | 4/2013 | Akiyama et al. |
| 8,432,171 B2 | 4/2013 | Coppe et al. |
| 8,436,629 B2 | 5/2013 | Chambon |
| 8,497,691 B2 | 7/2013 | Behle et al. |
| 8,505,443 B2 | 8/2013 | Abney et al. |
| 8,519,726 B2 | 8/2013 | Sun |
| 8,551,331 B2 | 10/2013 | Burkett et al. |
| 8,564,310 B2 | 10/2013 | Yu et al. |
| 8,614,588 B2 | 12/2013 | Hedges |
| 8,643,388 B2 | 2/2014 | Hedges |
| 8,689,679 B2 | 4/2014 | Tiszai et al. |
| 8,709,260 B2 | 4/2014 | Burkett et al. |
| 8,732,938 B2 | 5/2014 | Kolosov et al. |
| 8,736,282 B2 | 5/2014 | Chambon |
| 8,764,967 B2 | 7/2014 | Fan |
| 8,773,152 B2 | 7/2014 | Niemann et al. |
| 8,828,223 B2 | 9/2014 | Savage et al. |
| 8,829,928 B2 | 9/2014 | Gonzalez et al. |
| 8,847,120 B2 | 9/2014 | Burkett et al. |
| 8,854,058 B2 | 10/2014 | Katafuchi |
| 8,980,102 B2 | 3/2015 | Florkey et al. |
| 9,038,443 B1 | 5/2015 | Pace et al. |
| 9,161,659 B2 | 10/2015 | Lambert et al. |
| 9,170,144 B2 | 10/2015 | Qi |
| 9,176,086 B2 | 11/2015 | Qi |
| 9,228,965 B2 | 1/2016 | Burkett et al. |
| 9,510,708 B2 | 12/2016 | Behle et al. |
| 2002/0035931 A1 | 3/2002 | Tschopp et al. |
| 2002/0069767 A1 | 6/2002 | Wendel et al. |
| 2002/0082924 A1 | 6/2002 | Koether |
| 2004/0250622 A1 | 12/2004 | Kolosov et al. |
| 2005/0153022 A1 | 7/2005 | Schilling et al. |
| 2005/0247697 A1 | 11/2005 | Wu |
| 2006/0254432 A1 | 11/2006 | McLemore |
| 2007/0272209 A1 | 11/2007 | Matsiev et al. |
| 2008/0121578 A1 | 5/2008 | Burkett et al. |
| 2008/0196596 A1 | 8/2008 | Forrest et al. |
| 2008/0213446 A1 | 9/2008 | Feinberg et al. |
| 2008/0238445 A1 | 10/2008 | Muhl et al. |
| 2008/0282905 A1 | 11/2008 | Savage et al. |
| 2009/0044707 A1 | 2/2009 | Claesson et al. |
| 2009/0252842 A1 | 10/2009 | Wang et al. |
| 2009/0309619 A1* | 12/2009 | Behle .................. A47J 37/1223 324/698 |
| 2010/0000418 A1 | 1/2010 | Payen et al. |
| 2010/0201528 A1 | 8/2010 | Bruinsma et al. |
| 2010/0260903 A1 | 10/2010 | Wei et al. |
| 2011/0030486 A1 | 2/2011 | Hall et al. |
| 2011/0084708 A1 | 4/2011 | Yu |
| 2011/0234244 A1 | 9/2011 | Chambon |
| 2011/0238310 A1 | 9/2011 | Estrellado et al. |
| 2011/0267080 A1 | 11/2011 | Hedges |
| 2012/0022694 A1 | 1/2012 | Mohanty et al. |
| 2012/0062251 A1 | 3/2012 | Gonzalez et al. |
| 2012/0074125 A1 | 3/2012 | Burkett et al. |
| 2012/0075115 A1 | 3/2012 | Lee et al. |
| 2012/0229151 A1 | 9/2012 | Katafuchi |
| 2012/0229152 A1 | 9/2012 | Katafuchi |
| 2013/0036916 A1 | 2/2013 | Burkett et al. |
| 2013/0214797 A1 | 8/2013 | Gruden |
| 2013/0278276 A1 | 10/2013 | Behle et al. |
| 2014/0130579 A1 | 3/2014 | Hedges |
| 2014/0130900 A1 | 5/2014 | Hedges |
| 2014/0188404 A1 | 7/2014 | Von Herzen et al. |
| 2014/0188407 A1 | 7/2014 | Von Herzen et al. |
| 2014/0266065 A1 | 9/2014 | Von Herzen et al. |

(56) References Cited

U.S. PATENT DOCUMENTS

| | | | |
|---|---|---|---|
| 2015/0027205 | A1 | 1/2015 | Brugger |
| 2015/0272390 | A1 | 10/2015 | Burns et al. |
| 2015/0285777 | A1 | 10/2015 | Baumann et al. |

FOREIGN PATENT DOCUMENTS

| | | | |
|---|---|---|---|
| DE | 27 46 728 | | 4/1979 |
| DE | 82 3 081.5 | | 4/1990 |
| DE | 298 12 263 | U1 | 10/1998 |
| DE | 199 47 669 | A1 | 5/2001 |
| DE | 100 53 250 | A1 | 11/2002 |
| DE | 20 2005 007144 | U1 | 7/2005 |
| DE | 10 2005 039480 | A1 | 3/2007 |
| DE | 10 2006 003733 | B3 | 3/2007 |
| EP | 0 561 593 | A1 | 3/1993 |
| EP | 1 004 872 | A1 | 5/2000 |
| JP | 2003 250708 | A | 9/2003 |
| JP | 2005-055198 | A | 3/2005 |
| WO | WO 02/04914 | A2 | 1/2002 |
| WO | WO 2007/055980 | A1 | 5/2007 |
| WO | WO 2010/076839 | A2 | 7/2010 |
| WO | WO 2012/012747 | A2 | 1/2012 |
| WO | WO 2012/027304 | A1 | 3/2012 |
| WO | WO 2012/031924 | A1 | 3/2012 |
| WO | WO 2012/036964 | A2 | 3/2012 |
| WO | WO 2013/036813 | A1 | 3/2013 |
| WO | WO 2013/139354 | A1 | 9/2013 |
| WO | WO 2014/167158 | A1 | 10/2014 |
| WO | WO 2014/167159 | A1 | 10/2014 |
| WO | WO 2014/181209 | A1 | 11/2014 |
| WO | WO 2015/090359 | A1 | 6/2015 |
| WO | WO 2015/142283 | A1 | 9/2015 |
| WO | WO 2015/147886 | A1 | 10/2015 |

OTHER PUBLICATIONS

First Office Action in China Application No. 2015800437868, dated Aug. 8, 2018, 11 pp.
Deep Frying—Chemistry, Nutrition, and Practical Applications, $2^{nd}$ Edition, Michael D. Erickson, Editor, "Evaluation of Used Frying Oil" by Frank T. Orthoefer and Gary R. List, pp. 329-342, 19 pp.
Journal of Food Process Engineering, D.R. Heldman and R.P.Singh, CoEditors, Food & Nutrition Press, Inc., vol. 19, No. 2, Jun. 1996, "Dynamics of Fat/Oil Degradation During Frying Based on Physical Properties" by S. Paul and G. Mittal, pp. 201-221, 24 pp.
European Journal of Lipid Science and Technology, Official Journal of the European Federation for the Science and Technology of Lipids (Euro Fed Lipid), Special Topic: Deep Fat Frying—Healthier and Tastier Fried Food, Nov. 2004, "Tests to monitor quality of deep-frying fats and oils" by Richard F. Stier, pp. 766-771, www.ejlst.de, 9 pp.
Written Opinion of the International Searching Authority for PCT/US2015/037927, dated Oct. 8, 2015, 7 pp.
International Search Report for PCT/US2015/037927, dated Oct. 12, 2015, 4 pp.
English Translation of JP 2005-055198 for "Fat and Oil Degradation Detector and Fryer" submitted in IPR 2016-01435, 11 pp.
International Preliminary Report on Patentability for International Application No. PCT/US2015/037927, dated Jan. 3, 2017, 8 pp.
Written Opinion for PCT/US2016/061982, dated Jan. 17, 2017, 8 pp.
International Search Report for PCT/US2016/061982, dated Jan. 31, 2017, 2 pp.
International Search Report and Written Opinion for PCT/US2016/067179, dated May 12, 2017, 15 pp.
Communication from the Canadian Patent Office for Application No. 2,952,739, dated Nov. 1, 2017, 6 pp.

\* cited by examiner

SYSTEM AND METHOD FOR SENSING OIL QUALITY

CROSS-REFERENCE TO RELATED APPLICATIONS

This application is a continuation of U.S. Nonprovisional application Ser. No. 14/752,278, filed on Jun. 26, 2015, which claimed priority from U.S. Provisional Application No. 62/019,136, filed on Jun. 30, 2014, the entirety of which are each hereby incorporated by reference herein.

TECHNICAL FIELD

This disclosure relates to systems for measuring the quality of oil within a deep fat fryer system.

BRIEF SUMMARY

A first representative embodiment of the disclosure is provided. The embodiment includes a system for measuring the state of degradation of cooking oil in a deep fryer. The system includes at least one fryer pot and a loop of piping that is fluidly connected to said at least one fryer pot for selectively allowing a flow of oil from the at least one fryer pot into the loop and for selectively allowing the cooking oil to return to said at least one fryer pot from the loop. A pump is provided for urging the flow of cooking oil through the loop of piping and selectively to urge oil to return to the at least one fryer pot. The loop further comprises a first valve that is positionable to a closed position to prevent oil flow to or from the at least one fryer pot, and is positioned to an open position to allow flow to or from the at least one fryer pot. The loop further comprises a return portion that extends from a discharge of the pump toward a suction of the pump, wherein the return portion includes a second valve that is configured to selectively prevent or allow flow through the return portion. A sensor is disposed in fluid communication within the loop and adapted to measure an electrical property that is indicative of total polar materials of said cooking oil as the cooking oil flows within the loop of piping and past said sensor.

Another representative embodiment of the disclosure is provided. The embodiment includes a system for measuring the state of degradation of cooking oil in a deep fryer. The system includes at least one fryer pot and a loop of piping fluidly connected to said at least one fryer pot for selectively allowing flow of oil from the at least one fryer pot into the loop and for selectively allowing the cooking oil to return to said at least one fryer pot from the loop. A pump urges flow of cooking oil through the loop of piping and selectively to urge oil to return to the at least one fryer pot. The loop further comprises a first valve that is positionable to a closed position to prevent oil flow from the at least one fryer pot, and is positioned to an open position to allow flow from the at least one fryer pot. The loop further comprises a second valve that is positionable to a closed position to prevent oil flow to the at least one fryer pot, and is positioned to an open position to allow flow to the at least one fryer pot. The loop further comprises a recirculation portion that extends from a discharge of the pump toward a suction of the pump, wherein the recirculation portion includes a third valve that is configured to selectively prevent or allow flow through the recirculation portion. A sensor is disposed in fluid communication within the loop and adapted to measure an electrical property that is indicative of the quality of the cooking oil within the loop of piping, wherein the sensor is disposed in the recirculation portion of the loop. During cooking operations within the fryer pot the first and second valves are in the closed position, and during an operation of the sensor the first and second valves are shut.

Yet another representative embodiment of the disclosure is provided. The embodiment includes a method of calibrating a sensor used in conjunction with a deep fat fryer. The method includes the steps of providing a deep fat fryer including a frypot configured to receive a quantity of oil for cooking a food product disposed therein, and a loop of piping fluidly connected to said at least one fryer pot for selectively allowing flow of oil from the at least one fryer pot into the loop and for selectively allowing the cooking oil to return to the at least one fryer pot from the loop. A pump is provided for urging the flow of cooking oil through the loop of piping and to selectively urge oil to return to the at least one fryer pot, the loop further comprising a first valve disposed along a flow path from the fryer pot toward a suction of the pump, and a second valve disposed along a flow path from a discharge of the pump to the fryer pot. The loop further comprising a recirculation portion that extends from the discharge of the pump and toward a suction of the pump, wherein the recirculation portion includes a third valve that is configured to selectively prevent or allow flow through the return portion. A sensor is provided that is disposed in fluid communication with the loop and adapted to measure an electrical property that is indicative of the quality of the cooking oil within the loop of piping. The method includes the step of providing a controller that receives a signal from the sensor that is indicative of the electrical property measured by the sensor, and in use sending the signal from the sensor to the controller. The method additionally includes the step of providing a second sensor that is configured to interact with oil disposed within the deep fat fryer at a location remote from a position of the sensor with in the loop, wherein the second sensor is configured to measure the electrical property of the cooking oil that is indicative of the quality of the cooking oil, the second sensor is configured to send a second signal to the controller that is indicative of the measured electrical property by the second sensor. The controller is configured to compare the measurement of the second sensor received via the second signal with the measurement of the sensor received via the signal from the sensor and the controller is configured to modify a calibration of the sensor based upon a measured difference between the measurement by the sensor and the measurement by the second sensor.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
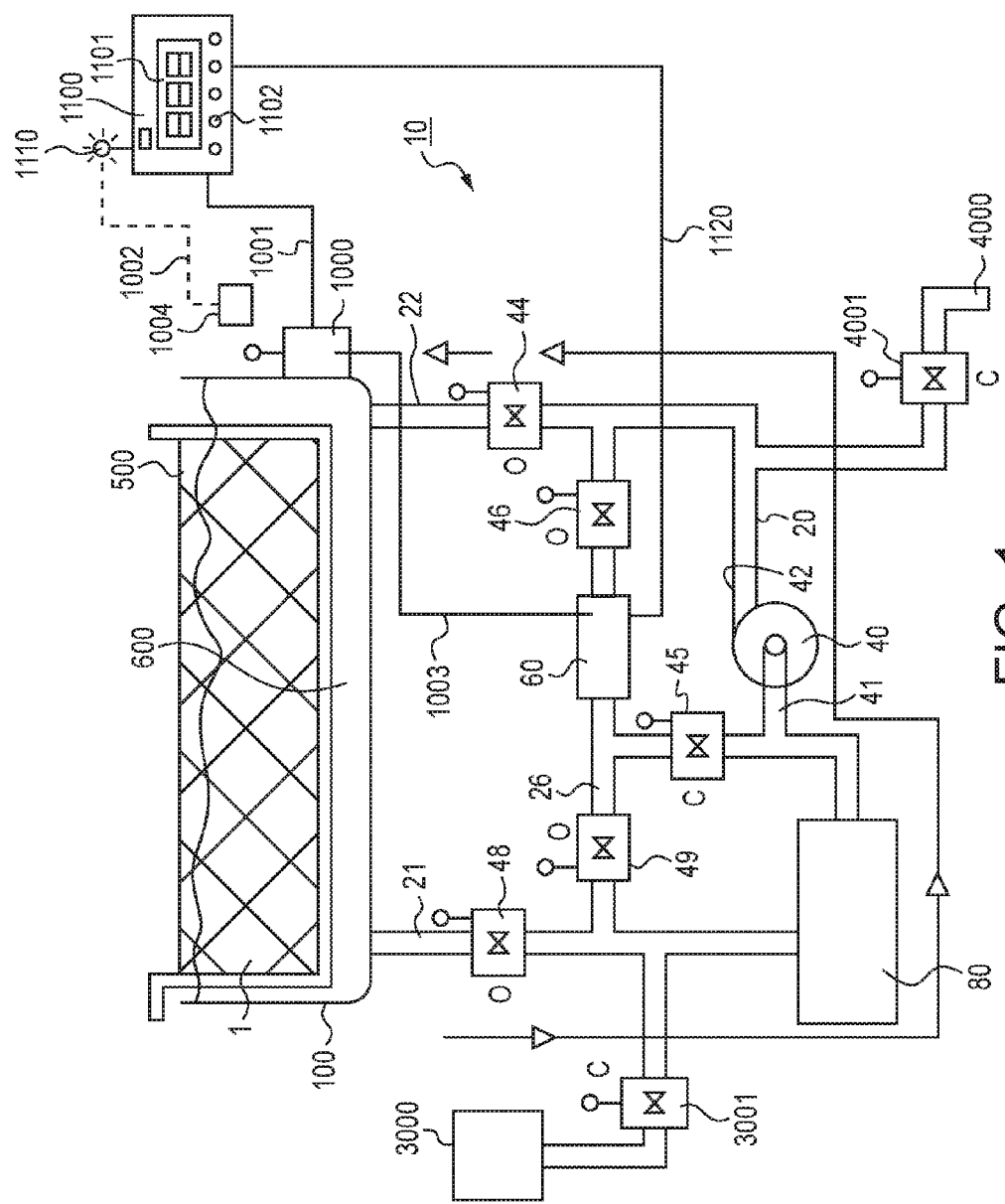
FIG. 1 is a first schematic view of a fryer with an oil sensing system.
Figure 2:
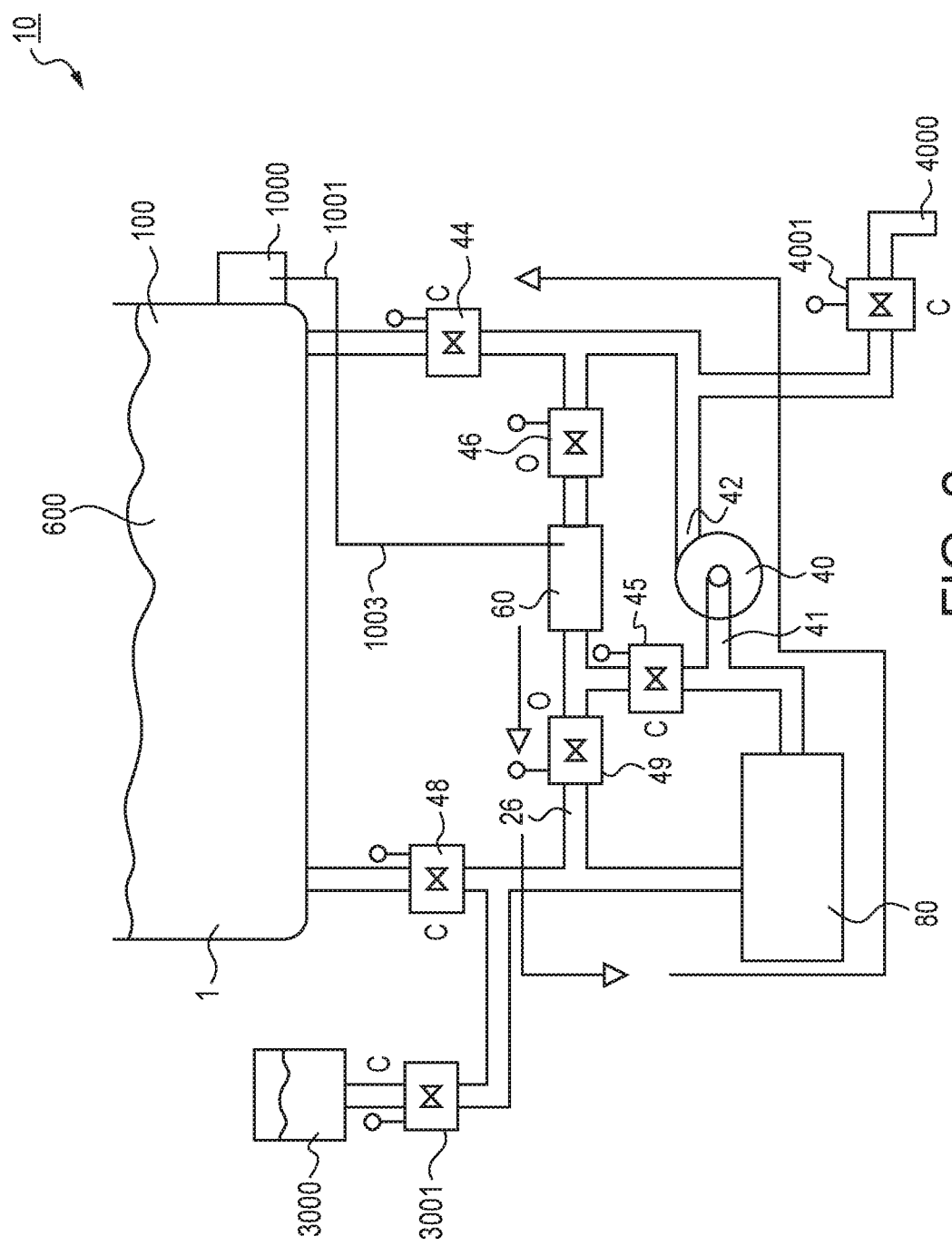
FIG. 2 is a schematic view of a fryer with a second oil sensing system.

Turning now to FIGS. 1-4, a system 10 for sensing the quality of oil in a deep fat fryer 1 is provided. The system 10 may be fluidly connected to a deep fat fryer 1, such that the system 10 can be either by continuously, cyclically, or manually used to measure the quality of oil located in the vat of the fryer, and can be operated during cooking operations of the fryer 10 or when cooking operations are not occurring in the fryer 10.

The system 10 may be fluidly connected to at least one fryer pot (frypot) 100, which is configured to hold a volume of oil, which is normally heated by one or more conventional electric heaters or gas burners which are in thermal communication with the frypot 100. The frypot 100 may be configured to receive one or more baskets 500 that are used to place food product within the heated oil to fry the food. With continued use, the oil within the frypot tends to become degraded through prolonged interaction with the food product as well as due to other factors, such as oxidation, hydrolysis, etc.

The frypot 100 may be fluidly connected to the system 10 with one or more oil outlets 21, and in some embodiments with one or more oil inlets 22. The system 10 may include a filter 80, a pump 40, a recirculation system 26, and an oil sensor 60, each discussed below. The system 10 may be formed as a loop 20 piping (such as rigid or flexible piping, or other types of conduit), that is configured to selectively allow the flow of oil from the at least one frypot 100, through the loop, and ultimately return to the at least one frypot 100 (FIG. 1). The system 10 may include a drain 4000, which may be controlled by a valve 4001 for selectively opening and closing the drain 4000. The valve 4001 may be a manual valve, or in some embodiments, the valve 4001 may be a remotely operated valve, such as a solenoid valve, and may be operable by a controller 1000. As discussed elsewhere herein, the controller 1000 may operate the drain valve 4001 for several reasons, such as to dump oil from the system 10 (and therefore the frypot 100), to "feed and bleed" oil (i.e. simultaneous dumping of oil from the drain 4000 and replacement with fresh oil from the storage vat 3000 (by operating the replacement valve 3001)). As discussed elsewhere herein, the controller 1000 may be programmed to automatically dump or feed and bleed oil from the system due to the measured quality of the oil by the sensor 60.

In some embodiments, the one or more oil outlets 21 from the frypot 100 may be selectively isolated by a valve 48 (or valves 48) that may be manual valves or remotely operable valves, such as solenoid valves. Similarly, the one or more oil inlets 22 to the frypot 100 may be selectively isolated by a valve 44 (or valves 44) that may be manual valves or remotely operable valves, such as solenoid valves.

The sensor 60 may be an electrical sensor that is adapted to continuously measure one or more electrical parameters of the oil which are directly indicative, or representative of the amount of impurities in the oil flowing through/past the sensor 60. For example, it is a well-known attribute of cooking oil to measure the total polar materials, or total polar compounds, therewithin and it is known that the amount of total polar materials/compounds increases as the life of the cooking oil decreases (i.e. the amount of total polar materials/compounds increases as the oil is used for longer time periods). The sensor 60 may be configured to continuously measure the capacitance of the oil flowing past/through the sensor, which is representative of the total polar materials/compounds in the oil, due to the known proportionality between the total polar materials/compounds in the oil and the dielectric constant of the oil. Still further, the sensor may be configured to measure voltage, resistance, dielectric, conductivity, or conductance of the oil, some or all of which may be indicative of total polar materials or other aspects of oil that relate to the overall quality of the oil, and in some embodiments, the sensor may be configured to measure more than one (or all) of these parameters.

The oil sensor may be a coaxial sensor, or a resonant sensor, or another type of sensor known in the art to be capable of sensing one or more electrical parameters of oil (such as those listed above) in order for the sensor to determine the total polar compounds/materials within the oil to allow for an oil quality determination to be made, such as by the controller 1000.

The sensor 60 may provide a signal 1003 to the controller 1000 that is indicative of the measured electrical property of the oil. In some embodiments, the controller 1000 may receive the signal 1003 and perform one or more of the functions discussed herein. For example, the controller 1000 may compare the measured electrical property of the oil to a programmed value (or range) of the electrical property. If the controller 1000 detects that the measured property is satisfactory (such as it is above or below a setpoint, or it is within a programmed acceptable range), the controller may provide an indication to the user that the oil quality is acceptable, such as through a readout 1101 on a display 1100 associated with the fryer, or on a remote device 1004 that communicates remotely 1002 (as schematically depicted in FIG. 1) with the controller 1000 (or display 1100), such as through WiFi, Bluetooth or another available remote communication means 1110.

In some embodiments, and as shown in FIG. 1, the sensor 60 may send an output signal 1120 directly to the display 1100.

In some embodiments where the sensor 60 may be multiple sensors that can simultaneously or non-simultaneously measure multiple different properties of oil, the user may control which property is sensed (or displayed) and the controller or the display may communicate with the sensor 60 to control the operation of the sensor, or otherwise direct the monitoring of the sensor. If the fryer is configured with an automated filtration system, the controller 1000 may send a signal to the automated filtration system that further filtration, or a batch filtration if the system is adapted for continuous filtration of a portion of the oil within the system, is unnecessary.

If the controller 1000 determines that the measured property is unsatisfactory (such as above a setpoint or within a range indicative of poor oil quality) the controller may provide an alarm to the user. The controller may also send a signal to an automated filtering system (when provided) indicating that a batch filter cycle is recommended (or perhaps required, such as immediately or after a current cooking cycle is completed). Further the controller 1000 could initiate an auto top-off system (when provided with the fryer) to automatically provide new oil to the frypot 100 and simultaneously open the drain valve 4001 to "feed and bleed" the poor quality oil with new oil, and potentially without interrupting cooking operations within the frypot. Moreover, if the measured property is above a setpoint, below a setpoint, or outside of an acceptable range, the controller could turn off the fryer (potentially when an in-process cooking cycle is completed) and cause an automatic draining (and disposal) of the frypot 100 and an automated refill of oil within the frypot (when an auto top-off system is provided), or automatically drain, and dispose of the oil and signal to the user that the frypot must be manually refilled.

The sensor 60 may be arranged to extend inline within the flow of oil through the system 10. In some embodiments, the sensor 60 may be disposed within a recirculation line 26 of the system 10, which is a line that extends generally between the discharge 42 of the pump 40 and the filter 80, and allows for oil to flow through the filter 80 and the pump without returning to the fryer pot 100. In some embodiments, the recirculation line 26 may include isolation valves 46, 49 on opposite sides of the sensor 60 (which may be manually or automatically controlled, such as by the controller 1000) such that the system 10 may be configured to isolate the sensor 60 and prevent oil flow therethrough, or configured to allow flow through the sensor 60. As discussed herein, the valves 44, 48 that selectively isolate the inlet and outlet 22, 21 of the frypot, respectively, may be controlled in conjunction with the operation of the sensor 60 within the recirculation system. For example, when the sensor 60 is operated in the recirculation system, the valves 44, 48 may be shut so that the pump 60 urges oil flow only through the recirculation system and the sensor 60 and the filter 80 (with the valve positions schematically depicted in FIG. 2, e.g. "O" for open, "C" for closed). This configuration might be useful to monitor the reduction of the capacitance (or the change in any other electrical characteristic discussed herein or otherwise known), and therefore total polar materials/compounds or any other electrical property of the oil monitored by the sensor 60 (discussed above), which could provide an indication of the operability or effectiveness of the filter 80 over time with continued flow.

Alternatively, in other embodiments, the sensor 60 may be operated with the valves 44 and 48 open (and with the recirculation line isolation valves 46, 49 open which allows for the oil from the frypot to be filtered continuously, as schematically depicted in FIG. 1, with the possible valve positions, "O" for open, "C" for closed) and the portion of the oil discharged from the pump 40 that runs through the recirculation line 26 (instead of returning to the frypot 100) measured. This type of operation would allow for continuous filtration and monitoring, if desired.

In some embodiments, the sensor 60 may be operated with the isolation valves 46, 49 shut, such that the sensor 60 would measure the electrical characteristic of the slug of oil disposed proximate to the sensor between the valves 46, 49. This configuration may be appropriate for sensors that more accurately measure an electrical characteristic of oil that is cooled significantly below normal cooking temperature of the oil. In some embodiments, the sensor 60 may be configured to measure the electrical characteristic of the oil that is either flowing past the sensor or relatively still (i.e. when the isolation valves 46, 49 are shut).

Figure 4:
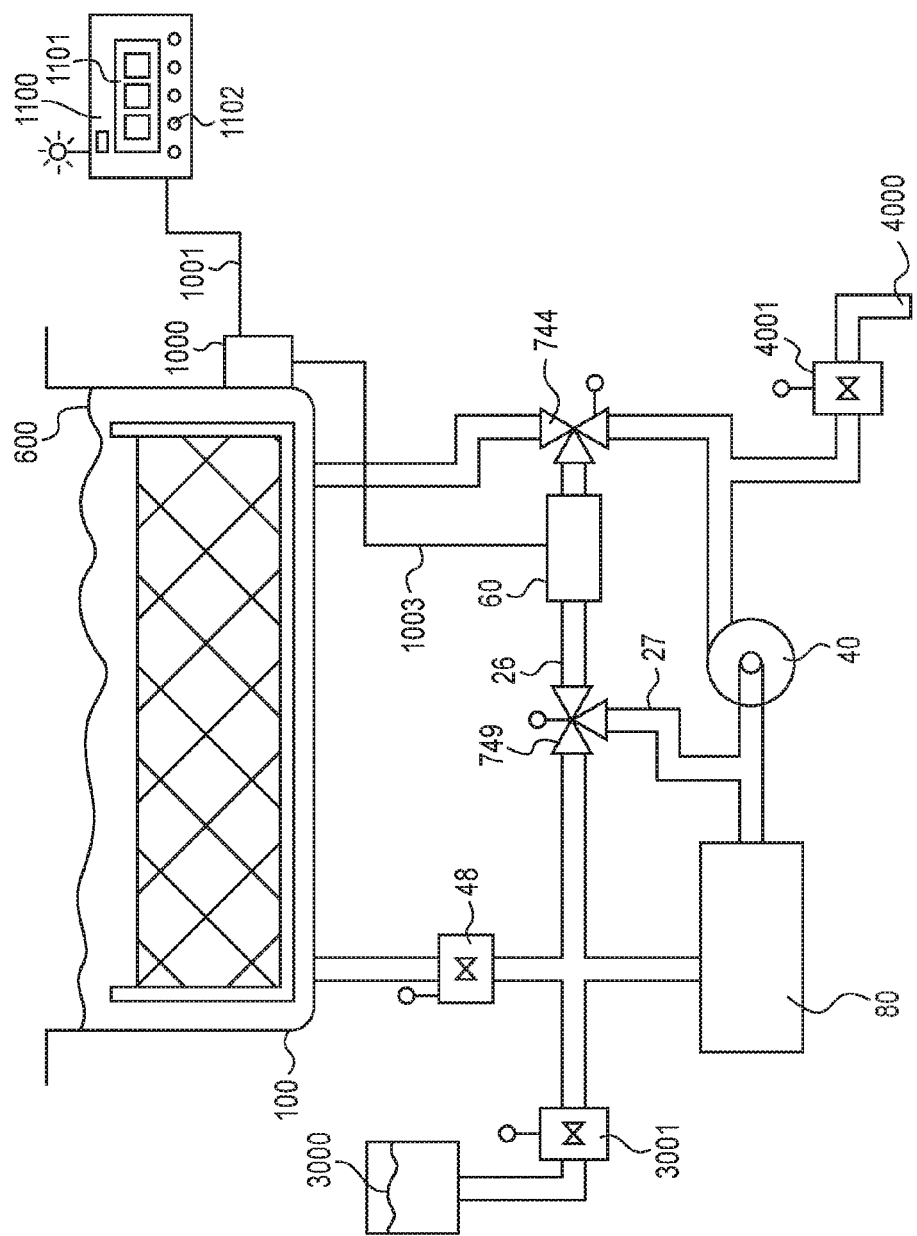
FIG. 4 is a schematic view of a fryer with another oil sensing system.

In some embodiments shown in FIG. 4, one or more of the valves discussed above and elsewhere herein may be replaced with three-way valves (744 or 749) that may be manually operated, remotely operated by the controller 1000 and/or automatically operated by the controller. For example, a three way valve 744 may be connected to each of the pump 40, the inlet of the fryer 22, and the recirculation line 26. The valve 744 may be configured to direct oil from the pump either to the frypot 100 through the return line, or to the recirculation line 26 (and the sensor 60). In some embodiments the valve 744 may be configured to allow flow from the pump 40 to both the frypot 100 through the return line and also to the recirculation line 26. In some embodiments, another three way valve 749 in the recirculation line 26 that is connected to piping downstream of the sensor 60, the piping that returns oil to the filter pan 80, as well as piping 27 that directs oil directly to the suction of the pump 40. As with valve 744, valve 749 may be manually operated, remotely operated by the controller 1000, and/or automatically operated by the controller 1000. The valve 749 may be configured to allow oil that flows through the sensor 60 to return to the filter pan 80, or to return directly to the pump 60 through line 27. In some embodiments, the valve 749 can be configured to block oil flowing from the sensor 60, which would cause oil in the recirculation 26 to be still within the sensor 60. In other embodiments, other three (or multiple way) valves may be provided, such as a three way valve that combines the frypot drain valve 48 and the replacement valve 3001, which would operate to selectively isolate the frypot 100 (to prevent oil from draining therefrom), and to selectively allow replacement oil into the filter pan 80. Other three valves could be used.

In some embodiments and as shown in FIG. 1, in some embodiments, the loop may include a pipe 27 that extends from downstream of the sensor 60, but before the downstream isolation valve 49 directly to the suction of the pump 40 (or alternatively downstream of the downstream isolation valve 49), therefore allowing flow through the sensor 60 that bypasses the filter 80. In some embodiments the pipe 27 may be selectively isolated by a valve 45.

Figure 3:
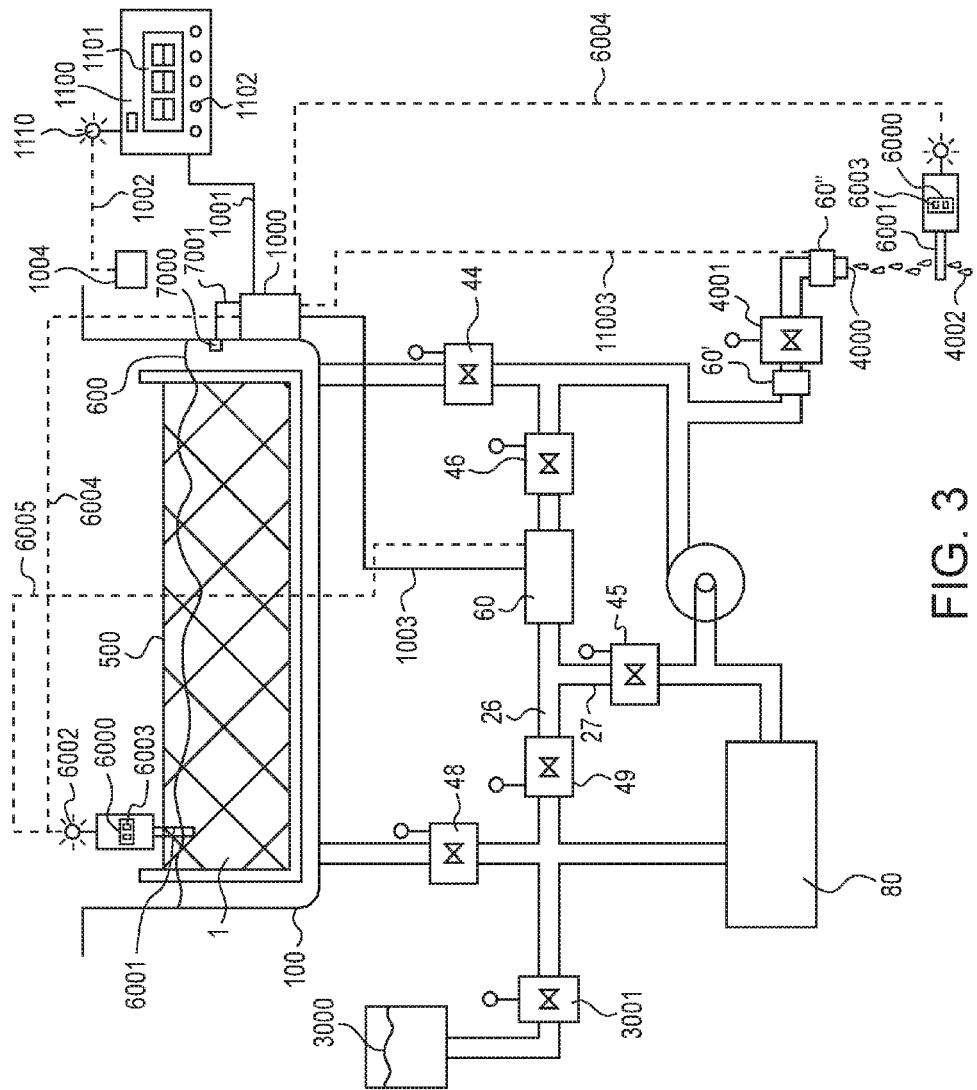
FIG. 3 is a schematic view of a fryer with the oil sensing system of FIG. 1 with a calibration system.

In some embodiments depicted in FIG. 3, a sensor (60' or 60") may be provided in the drain line 4000 that allows for the oil to be disposed from the loop and ultimately from the fryer to be measured, in a similar manner to the sensor 60, discussed above. The sensor 60' (depicted upstream of the drain valve 4001) or the sensor 60" (positioned downstream of the drain valve 4001) may communicate with the controller 1000 via a signal 11003, with the controller 1000 operating with respect to the sensor 60' or 60" in the same manner as the sensor 60 as discussed herein, including the calibration functionality as discussed herein. One of ordinary skill in the art will understand that the sensor 60' or 60" may be beneficial to the operator to inform the operator of the quality (i.e. the value of the measured electrical property of the oil that is indicative of the quality of the oil) that is being drained from the fryer, which might be useful such as in situations where it is impractical or undesirable to send oil through the recirculation line 26 for a measurement by the sensor 60.

The filter 80 may be one of many types of filter systems known in the art. For example, the filter may be a batch filter system, which generally includes a filter vat 80, and one or more filter screens or meshes or filter papers that are configured to mechanically particulate matter (such as crumbs) and impurities that normally collect in oil after extended cooking of food product as well as after extended time at the cooking temperature due to oxidation, hydrolysis or other phenomenon. With a batch filtering process, oil, when not actively cooking a food product within the frypot 100, is drained to the filter vat 80, such that the oil passes through the various filtering screens or other filtering members. The filter vat 80 is normally filled when oil is drained from the frypot 100 through valve 48. The pump 40 draws a suction from the filter vat 80 and urges the oil within the filter vat to flow through the filtering media and out of the filtering vat 80 where it is pumped within the system.

Alternatively, the system may be used with a continuous filtering system. In such a system, volume of oil 600 from the frypot 100 flows (either naturally or with a pump (not shown)) out of the frypot 100 and into the filtering system, where the oil flows through the filter vat 80 and is ultimately pumped through the system, either returning to the frypot 100 or through the recirculation line 26 and the sensor 60. One of ordinary skill in the art with a thorough review of the subject specification and figures will readily contemplate how to construct an appropriate batch filtering system or an appropriate continuous filtering system that is configured to be readily used with an oil quality sensor 60 disposed within a recirculation line. One of ordinary skill in the art would understand that such an alignment for an oil sensor 60, especially with a batch filtering system, would be beneficial, such as for evaluation of the performance of the oil filter 80.

For example, the operator (or a controller) could monitor the output of the oil sensor 60 as the pump 40 operates (with oil drained from the frypot 100 and into the filter vat 80 and filtering system 10). If the pump 40 is run continuously for a set period of time, and the valves 44, 48 are shut, the operator (or controller 1000) can measure the electrical property of the oil (such as a property of total polar materials as discussed above or any other property of oil capable of continuous monitoring), as monitored by the sensor 60 over time. If the sensed property improves (such as through an "improvement" of a parameter that is measured by the sensor over time toward a range or an optimum level, which is an indication that the oil's ability to effectively and efficiently cook foods is improving) over time, it may be determined the filter 80 is operating properly. If the measured property of the oil does not improve over time, then the filter 80 may not be working properly. One of ordinary skill in the art will also contemplate that the rate of change of oil quality may also be an indication of the operability of the filter 80.

Turning now to FIG. 3, a system for calibration of the sensor 60 that is provided within the recirculation line 26 of the fryer 1 is provided. The system may include all of the components of the filter system and the recirculation system discussed above, such as a filter pan 80, loop isolation valves 44, 46, a sensor 60, and recirculation line isolation valves 46, 49. The system may further include a controller 1000, which, as discussed above, may receive a signal 1003 from the sensor 60 that is indicative of the measured electrical property of the oil. In some embodiments the signal 1003 may be a raw digital or analog signal (such as a voltage that changes based upon the magnitude of the measured parameter) that is representative of the measurement taken by the sensor 60, with the controller 1000 receiving the raw signal and converting it to a measured property. In other embodiments, the signal 1003 may be a signal that is the value of the actual parameter being measured. In other words, in some embodiments, the sensor 60 may supply a signal 1003 that must be processed and analyzed by the controller to determine the value of the parameter being measured (conductivity, dielectric constant, etc.), and in some embodiments evaluated by the controller 1000 to determine whether a signal, indication, or alarm should be provided to the user (through signal 1001).

In either of the above possibilities initial and/or periodic or routine calibration of the sensor 60 must be performed to ensure that the measured electrical property (by the sensor 60) is indicative of the same electrical property of the actual oil. It is known in the art that the electrical characteristics of sensors (and processing equipment) may vary over time based upon factors such as changing internal resistance, fouling of the surface of a sensor's electrodes, or for other reasons. Due to these or any other changes in the sensor's operation (or possibility changes in the wiring or path for an analog signal transmission to the controller), it is important to periodically assess the proper operation of the sensor and recalibrate the sensor as necessary.

For example, in some embodiments, a portable sensor 6000 (shown schematically in FIG. 3) that measures the same electrical property of the oil as measured by the sensor may be provided. The sensor 6000 may include a probe 6001 may be used to measure the electrical characteristic of the oil 600 within the fryer pot 100, and/or in other embodiments the portable sensor 6000 may be used to measure the electrical characteristic of the oil 600 within another position within the fryer 10, such as oil flowing (4002) from the drain 4000 (also shown schematically in FIG. 3). The portable sensor 6000 may provide a direct reading of the measured electrical characteristic upon its display 6003. Alternatively or additionally, the portable sensor 6000 may provide a signal 6004 to the controller 1000 that is representative of the measured electrical characteristic (either the signal 6004 being the actual value of the measured electrical characteristic, or a measurement that is representative of the measured characteristic, similar to the sensor 60 as discussed above). In embodiments where the portable sensor 6000 is used, assuming that the calibration of the portable sensor 6000 was recently verified, the controller 1000 receives the value of the measured parameter via the signal 6004 and compares the measured parameter from the portable sensor 6000 with the value of the measured parameter from the sensor 60 as received by the controller 1000. If there is any difference between the values of the measured parameter from the portable sensor 6000 and the sensor 60, the controller 1000 can automatically adjust the gain (or another adjustable parameter) of the sensor 60 to calibrate the output of the sensor 60, or alternatively or additionally modify the controller's processing of the signal 1003 received from the sensor 60 such that the value of the measured parameter of the sensor 60 is consistent with the measured value of the sensor 6000, in order for the measurement taken by the sensor 60 to reflect the "accurate" measurement of the same parameter using the portable sensor 6000.

Various calibration techniques that could be implemented by the controller 1000 to adjust the calibration of the sensor 60 (such adjusting the gain, or the input voltage of the sensor 60) are well known in the art and will not be repeated herein for the sake of brevity. In some embodiments, the adjustment could be made to the operation of the sensor 60, such as adjusting the gain of the sensor, which would result in the sensor 60 sending a differing signal 1003 to the controller after the adjustment, while in other embodiments, the calibration may occur within the controller 1000, such that the controller changes the way that the signal 1003 received from the sensor 60 is processed to result in the value of the measured parameter as calculated by the controller 1000. In some embodiments where the calibration changes are made directly to the sensor's 60 operation, the changes (or instructions for the sensor 60 to change) are sent to the sensor 60 automatically via the signal path 1003.

Alternatively, the controller 1000 may generate and provide the user with instructions to manually adjust the sensor 60 to properly calibrate the sensor. The instructions may be via a display 1100 upon the fryer, or a message that is relayed to the user via wireless communication, WiFi, Bluetooth, and via different types of information exchange methods (email, text, etc.).

In some embodiments, the controller 1000 may store calibration events, and in some embodiments index calibration events, such as with a date/time stamp, for future reference. In some embodiments, when a measurement of an electrical parameter of the oil by the sensor 60 is outside of a specification, or the controller detects a moving trend in the measured parameter by the sensor 60, the controller may reference the calibration history of the sensor 60, and suggest to the user that a calibration may be called for (using the portable sensor 6000), before or in conjunction with the controller 1000 taking action with respect to the oil, such as automatically initiating a filter event, dumping oil through the drain 4000, or feeding and bleeding oil, or the like.

In other embodiments, the portable sensor 6000 may communicate with the sensor 60 directly (such as via a signal path 6005 shown schematically in FIG. 3), in addition to or instead of the communication with the controller 1000. In these embodiments, the sensor 60 may be programmed to self-calibrate based upon the signal received from the portable sensor 6000, rather than be calibrated based upon instructions received from the controller 1000. Other than this difference, the calibration of the sensor 60 based upon signals received from the portable sensor 6000 is consistent with the embodiments described above.

In some embodiments, as shown in FIG. 3, the fryer 1 may include one or more oil quality sensors 7000 that are positioned to monitor a desired parameter of oil within the fryer pot 100 (or within one fryer pot 100 of a fryer set up where multiple neighboring fryer pots 100 are fluidly connected to one filtration system and oil sensor 60 disposed within a recirculation line 26 within a filtration system). The one or more oil quality sensors 7000 may be configured to measure the same parameter of oil as the sensor 60 that is positioned in the recirculation line 26, while in other embodiments, one or more sensors 7000 may be configured to measure a different parameter of oil as the sensor 60. The one or more sensors 7000 may communicate with the controller 1000 via a path 7001, which may be hard wired or wireless. In other embodiments, other than the difference between the sensor 7000 which may be rigidly mounted upon the fryer pot 100 to directly (or indirectly) measure one or more electrical characteristics of the oil within the fryer pot, the operation of the sensor 7000 and the method for calibration of the sensor 60 based upon a measurement by the sensor 7000 is consistent with the description of the operation and calibration based upon the portable sensor 6000 described above. In some embodiments, the sensor 7000 provides the measurement(s) of the electrical parameters of oil quality to the controller, with any automated operations of the fryer from the controller 1000, or indications to the user regarding oil quality based upon the measurements taken from sensor 7000. In some embodiments, the portable sensor 6000 (discussed elsewhere herein) may be used for calibrating the sensor 7000, in the same manner as discussed herein with respect to the calibration of sensor 60.

The following numbered paragraphs are provided:

Numbered Paragraph 1: A system for measuring the state of degradation of cooking oil in a deep fryer comprising:
at least one fryer pot;
a loop of piping fluidly connected to said at least one fryer pot for selectively allowing flow of oil from the at least one fryer pot into the loop and for selectively allowing the cooking oil to return to said at least one fryer pot from the loop;
a pump for urging the flow of cooking oil through the loop of piping and selectively to urge oil to return to the at least one fryer pot,
the loop further comprising a first valve that is positionable to a closed position to prevent oil flow to or from the at least one fryer pot, and is positioned to an open position to allow flow to or from the at least one fryer pot,
the loop further comprises a return portion that extends from a discharge of the pump toward a suction of the pump, wherein the return portion includes a second valve that is configured to selectively prevent or allow flow through the return portion;
a sensor disposed in fluid communication within the loop and adapted to measure an electrical property that is indicative of the quality of the cooking oil within the loop of piping, wherein the sensor is disposed in the return portion of the loop.

Numbered Paragraph 2: The system of numbered paragraph 1, wherein the sensor is configured to measure an electrical property that is indicative of the total polar materials of the cooking oil.

Numbered Paragraph 3: The system of numbered paragraph 1, wherein the sensor is configured to measure the electrical property of the cooking oil when the cooking oil flows past the sensor.

Numbered Paragraph 4: The system of numbered paragraph 1, wherein the sensor is configured to measure the electrical property of the cooking oil when the cooking oil is relatively stationary next to the sensor.

Numbered Paragraph 5: The system of numbered paragraph 1, wherein the sensor is configured to measure the electrical property of the cooking oil when the cooking oil flows past the sensor and when the cooking oil is relatively stationary next to the sensor.

Numbered Paragraph 6: The system of numbered paragraph 1, wherein said sensor is selected from a capacitance sensor, a voltage sensor, a resistance sensor, a dielectric sensor, a conductivity sensor, or a conductance sensor.

Numbered Paragraph 7: The system of numbered paragraph 1, wherein said sensor is a coaxial sensor.

Numbered Paragraph 8: The system of numbered paragraph 1, further comprising an oil filtration system that is disposed in fluid communication with the loop.

Numbered Paragraph 9: The system of numbered paragraph 1, wherein the first valve is located downstream from a discharge of the pump.

Numbered Paragraph 10: The system of numbered paragraph 1, wherein the sensor is configured to measure two or more of capacitance, voltage, resistance, dielectric, conductivity, or conductance of oil that contacts the sensor.

Numbered Paragraph 11: The system of numbered paragraph 1, wherein the sensor is disposed upstream of a suction of the pump.

Numbered Paragraph 12: The system of numbered paragraph 1, further comprising a controller that receives a signal from the sensor indicative of the measured electrical property of the oil.

Numbered Paragraph 13: The system of numbered paragraph 12, wherein the first and second valves are remotely operable by the controller, and the controller is configured to selectively operate one or both of the first and second valves based upon the measured electrical property of the oil.

Numbered Paragraph 14: The system of numbered paragraph 13, wherein the loop is fluidly connected to a source of replacement oil, and wherein the loop further comprises a drain, wherein the controller is configured to selectively open the drain to allow cooking oil within the loop to drain from the loop and to selectively allow replacement oil to flow into the loop, wherein the controller selectively allows the cooking oil to drain from the loop and allows replacement oil to flow into the loop based upon the measured electrical property of the oil.

Numbered Paragraph 15: The system of numbered paragraph 1, further comprising a third valve positioned within the return portion and located between the sensor and an oil filtration system, such that oil flowing through the return portion flows first through the sensor, then through the third valve, and then into the oil filtration system.

Numbered Paragraph 16: The system of numbered paragraph 15, wherein the third valve is operable by a controller, wherein the third valve is opened when the second valve is opened by the controller, and the third valve is shut when the second valve is shut by the controller.

Numbered Paragraph 17: The system of numbered paragraph 1, further comprising a display or an alarm in electrical communication with said sensor for indicating a parameter of the oil that is representative of the measured electrical property of the oil.

Numbered Paragraph 18: The system of numbered paragraph 1, wherein the loop is connected to the fryer pot with a first connection that is in fluid communication with a suction of the pump and the loop is connected to the fryer pot with a second connection that is in fluid communication with a discharge of the pump, wherein the first valve is disposed upon the first connection, and further comprising a third valve that is disposed between the discharge of the pump and the fryer pot.

Numbered Paragraph 19: The system of numbered paragraph 12, further comprising a second sensor, the second sensor being configured to interact with oil disposed within the deep fat fryer at a location remote from the return portion, wherein the second sensor is adapted to measure the electrical property of the cooking oil that is indicative of the quality of the cooking oil, that is measured by the sensor, wherein the second sensor is configured to send a signal to the controller that is representative of the measurement of the electrical property of the cooking oil by the second sensor, and the controller is configured to compare the measurement of the second sensor with a measurement of the electrical property of the cooking oil received from the sensor, and the controller is configured to modify a calibration of the sensor based upon a determined difference between the measurement by the sensor and the measurement by the second sensor.

Numbered Paragraph 20: The system of numbered paragraph 19, wherein the controller is configured to send a signal to the sensor to modify a setting of the sensor to modify the calibration of the sensor.

Numbered Paragraph 21: The system of numbered paragraph 19, wherein the controller is configured to adjust its settings for processing a signal received from the sensor that is indicative of the quality of the cooking oil within the loop of piping to modify the calibration of the sensor.

Numbered Paragraph 22: The system of numbered paragraph 19, wherein the second sensor sends the signal to the controller wirelessly.

Numbered Paragraph 23: A system for measuring the state of degradation of cooking oil in a deep fryer comprising:
at least one fryer pot;
a loop of piping fluidly connected to said at least one fryer pot for selectively allowing flow of oil from the at least one fryer pot into the loop and for selectively allowing the cooking oil to return to said at least one fryer pot from the loop;
a pump for urging the flow of cooking oil through the loop of piping and selectively to urge oil to return to the at least one fryer pot,
the loop further comprising a first valve that is positionable to a closed position to prevent oil flow from the at least one fryer pot, and is positioned to an open position to allow flow from the at least one fryer pot,
the loop further comprising a second valve that is positionable to a closed position to prevent oil flow to the at least one fryer pot, and is positioned to an open position to allow flow to the at least one fryer pot,
the loop further comprises a recirculation portion that extends from a discharge of the pump toward a suction of the pump, wherein the recirculation portion includes a third valve that is configured to selectively prevent or allow flow through the recirculation portion;
a sensor disposed in fluid communication within the loop and adapted to measure an electrical property that is indicative of the quality of the cooking oil within the loop of piping, wherein the sensor is disposed in the recirculation portion of the loop,
wherein during cooking operations within the fryer pot the first and second valves are in the closed position, and during an operation of the sensor the first and second valves are shut.

Numbered Paragraph 24: The system of numbered paragraph 23, further comprising a fourth valve positioned within the recirculation portion and disposed on an opposite side of the sensor from the third valve.

Numbered Paragraph 25: The system of numbered paragraph 24, wherein the third and fourth valves are open during operation of the sensor.

Numbered Paragraph 26: The system of numbered paragraph 24, wherein the third and fourth valves are shut during operation of the sensor.

Numbered Paragraph 27: The system of numbered paragraph 23, wherein the sensor is configured to measure an electrical property that is indicative of the total polar materials of the cooking oil.

Numbered Paragraph 28: The system of numbered paragraph 23, wherein the sensor is selected from a capacitance sensor, a voltage sensor, a resistance sensor, a dielectric sensor, a conductivity sensor, or a conductance sensor.

Numbered Paragraph 29: The system of numbered paragraph 23, further comprising a controller that receives a signal from the sensor indicative of the measured electrical property of the oil.

Numbered Paragraph 30: The system of numbered paragraph 29, wherein the first and second valves are remotely operable by the controller, and the controller is configured to selectively operate one or both of the first and second valves based upon the measured electrical property of the oil.

Numbered Paragraph 31: The system of numbered paragraph 30, wherein the loop is fluidly connected to a source of replacement oil, and wherein the loop further comprises a drain, wherein the controller is configured to selectively open the drain to allow cooking oil within the loop to drain from the loop and to selectively allow replacement oil to flow into the loop, wherein the controller selectively allows the cooking oil to drain from the loop and allows replacement oil to flow into the loop based upon the measured electrical property of the oil.

Numbered Paragraph 32: The system of numbered paragraph 29, further comprising a second sensor, the second sensor being configured to interact with oil disposed within the deep fat fryer at a location remote from the recirculation portion, wherein the second sensor is adapted to measure the electrical property of the cooking oil that is indicative of the quality of the cooking oil that is measured by the sensor, wherein the second sensor is configured to send a second signal to the controller that is representative of the measurement of the electrical property of the cooking oil by the second sensor, and the controller is configured to compare the measurement of the second sensor received via the second signal with a measurement of the electrical property of the cooking oil received from the sensor via the signal, and the controller is configured to modify a calibration of the sensor based upon a measured difference between the measurement by the sensor and the measurement by the second sensor.

Numbered Paragraph 33: The system of numbered paragraph 32, wherein the controller is configured to send a signal to the sensor to modify a setting of the sensor to modify the calibration of the sensor.

Numbered Paragraph 34: The system of numbered paragraph 32, wherein the controller is configured to adjust its settings for processing a signal received from the sensor that is indicative of the quality of the cooking oil within the loop of piping to modify the calibration of the sensor.

Numbered Paragraph 35: The system of numbered paragraph 32, wherein the second sensor sends the signal to the controller wirelessly.

Numbered Paragraph 36: A method of calibrating a sensor used in conjunction with a deep fat fryer, comprising:
  providing a deep fat fryer including a fryer pot configured to receive a quantity of oil for cooking a food product disposed therein, and a loop of piping fluidly connected to said at least one fryer pot for selectively allowing flow of oil from the at least one fryer pot into the loop and for selectively allowing the cooking oil to return to the at least one fryer pot from the loop, a pump for urging the flow of cooking oil through the loop of piping and to selectively urge oil to return to the at least one fryer pot, the loop further comprising a first valve disposed along a flow path from the fryer pot toward a suction of the pump, and a second valve disposed along a flow path from a discharge of the pump to the fryer pot,
  the loop further comprising a recirculation portion that extends from the discharge of the pump and toward a suction of the pump, wherein the recirculation portion includes a third valve that is configured to selectively prevent or allow flow through the recirculation portion,
  providing a sensor disposed in fluid communication with the loop and adapted to measure an electrical property that is indicative of the quality of the cooking oil within the loop of piping,
  providing a controller that receives a signal from the sensor that is indicative of the electrical property measured by the sensor, and in use sending the signal from the sensor to the controller,
  providing a second sensor that is configured to interact with oil disposed within the deep fat fryer at a location remote from a position of the sensor within the loop, wherein the second sensor is configured to measure the electrical property of the cooking oil that is indicative of the quality of the cooking oil that is measured by the sensor, the second sensor is configured to send a second signal to the controller that is indicative of the measured electrical property by the second sensor;
  wherein the controller is configured to compare the measurement of the second sensor received via the second signal with the measurement of the sensor received via the signal from the sensor,
  wherein the controller is configured to modify a calibration of the sensor based upon a measured difference between the measurement by the sensor and the measurement by the second sensor.

Numbered Paragraph 37: The method of numbered paragraph 36, wherein the sensor is disposed within the recirculation portion of the loop.

Numbered Paragraph 38: The method of numbered paragraph 36, wherein the second sensor is configured to send a wireless signal to the controller that is the second signal.

Numbered Paragraph 39: The method of numbered paragraph 36, wherein the recirculation portion of the loop comprises a third valve that is disposed between the discharge of the pump and the sensor, and wherein the controller is configured to open the third valve when a sensing operation by the sensor is desired.

While the preferred embodiments of the disclosed have been described, it should be understood that the invention is not so limited and modifications may be made without departing from the disclosure. The scope of the disclosure is defined by the appended claims, and all devices that come within the meaning of the claims, either literally or by equivalence, are intended to be embraced therein.

The invention claimed is:

1. A system for measuring the state of degradation of cooking oil in a deep fryer comprising:
   at least one fryer pot, comprising an oil inlet and an oil outlet;
   a loop of piping connected to said at least one fryer pot for selectively allowing flow of oil from the at least one fryer pot through the oil outlet into the loop and for selectively allowing the cooking oil to return to said at least one fryer pot through the oil inlet from the loop;
   a pump for urging the flow of cooking oil through the loop and selectively to urge oil to return to the at least one fryer pot through the oil inlet,
   the loop further comprising a first valve that is positionable in an isolated position to prevent oil flow from returning to the at least one fryer pot through the oil inlet, and is positionable in a second position to allow oil to return to flow the at least one fryer pot through the oil inlet,
   the loop further comprises a recirculation portion that extends from a discharge of the pump toward a suction of the pump, wherein the recirculation portion extends from a first portion that selectively receives oil flow from the discharge of the pump to a second portion that is fluidly connected with a suction of the pump;
   a sensor disposed in the recirculation portion and adapted to measure an electrical property that is indicative of the quality of the cooking oil within the loop of piping,
   wherein the recirculation portion is configured to allow oil to flow past the sensor as urged by the pump with the first valve in the isolated position,
   wherein the sensor is configured to measure an electrical property that is indicative of the total polar materials of the cooking oil and is configured to measure the electrical property of the cooking oil when the cooking oil flows past the sensor, and
   further comprising a display or an alarm in electrical communication with said sensor for indicating a parameter of the oil that is representative of the measured electrical property of the oil.

2. The system of claim 1, wherein the sensor is configured to measure the electrical property of the cooking oil when the cooking oil flows past the sensor and when the cooking oil is relatively stationary next to the sensor.

3. The system of claim 1, wherein said sensor is selected from a capacitance sensor, a voltage sensor, a resistance sensor, a dielectric sensor, a conductivity sensor, or a conductance sensor.

4. The system of claim 1, wherein said sensor is a coaxial sensor.

5. The system of claim 1, further comprising an oil filtration system that is disposed in fluid communication with the loop and with the second end portion of the recirculation portion such that oil flowing through the recirculation portion and past the sensor reaches the oil filtration system, wherein the suction of the pump is fluidly connected with the oil filtration system.

6. The system of claim 1, wherein the first valve is located downstream from the discharge of the pump.

7. The system of claim 1, wherein the sensor is configured to measure two or more of capacitance, voltage, resistance, dielectric, conductivity, or conductance of oil that contacts the sensor.

8. The system of claim 1, wherein the sensor is disposed upstream of the suction of the pump.

9. The system of claim 1, wherein the loop includes a second valve that is positionable to selectively prevent or allow flow through the recirculation portion, wherein the second valve is disposed between the discharge of the pump and the sensor.

10. The system of claim 9, further comprising a controller that receives a signal from the sensor indicative of the measured electrical property of the oil.

11. The system of claim 10, wherein the first and second valves are remotely operable by the controller, and the controller is configured to selectively operate one or both of the first and second valves based upon the measured electrical property of the oil.

12. The system of claim 11, wherein the loop is fluidly connected to a source of replacement oil, and wherein the loop further comprises a drain, wherein the controller is configured to selectively open the drain to allow cooking oil within the loop to drain from the loop and to selectively allow replacement oil to flow into the loop, wherein the controller selectively allows the cooking oil to drain from the loop and allows replacement oil to flow into the loop based upon the measured electrical property of the oil.

13. The system of claim 9, further comprising a third valve positioned within the recirculation portion and located between the sensor and an oil filtration system, wherein the third valve is downstream of the sensor and the second valve, such that oil flowing through the recirculation portion flows through the sensor, then through the third valve, and then into the oil filtration system.

14. The system of claim 13, wherein the third valve is operable by a controller, wherein the third valve is opened when the second valve is opened by the controller, and the third valve is closed when the second valve is closed by the controller.

15. The system of claim 1, wherein the first valve is a three way valve that is disposed between the discharge of the pump and the oil inlet of the frypot and the first valve is additionally connected with the recirculation portion, and wherein when the first valve is positioned in the second position the three way valve is aligned to direct oil flowing therethrough into the oil inlet of the frypot, and when the first valve is positioned in the isolated position the three way valve is aligned to direct oil flowing therethrough into the recirculation portion of the loop.

16. The system of claim 1, wherein the first valve is closed when in the isolated position.

17. The system of claim 1, wherein the first valve is aligned to direct flow from the pump discharge to the recirculation portion when in the isolated position.

* * * * *

UNITED STATES PATENT AND TRADEMARK OFFICE
CERTIFICATE OF CORRECTION

PATENT NO.         : 10,178,927 B2
APPLICATION NO.    : 15/863197
DATED              : January 15, 2019
INVENTOR(S)        : McGhee et al.

Page 1 of 1

It is certified that error appears in the above-identified patent and that said Letters Patent is hereby corrected as shown below:

In the Claims

At Claim 1, Column 14, Line 41, please insert --to-- after "flow" and before "the"

Signed and Sealed this
Twelfth Day of March, 2019

Andrei Iancu
*Director of the United States Patent and Trademark Office*